(12) United States Patent
Domeier et al.

(10) Patent No.: US 7,101,358 B2
(45) Date of Patent: Sep. 5, 2006

(54) TAMPON WRAPPER WITH OPENING MEANS COMPRISING STOPPER

(75) Inventors: Wolfgang Werner Hans Domeier, Kreuzau-Drove (DE); Charles John Berg, Jr., Wyoming, OH (US); Ricky Alan Pollard, Moscow, OH (US); Francis Michael Nicholas, Addlestone (GB); Paul Lee Styles, Waterlooville (GB); Conrad Eckhardt, Frankfurt am Main (DE)

(73) Assignee: The Procter & Gamble Company, Cincinnati, OH (US)

( * ) Notice: Subject to any disclaimer, the term of this patent is extended or adjusted under 35 U.S.C. 154(b) by 488 days.

(21) Appl. No.: 10/154,293

(22) Filed: May 23, 2002

(65) Prior Publication Data

US 2003/0220625 A1 Nov. 27, 2003

(51) Int. Cl.
*A61F 13/20* (2006.01)
*B65D 85/08* (2006.01)
*B65D 75/00* (2006.01)

(52) U.S. Cl. .............. 604/385.02; 206/824; 206/440

(58) Field of Classification Search .......... 206/226, 206/229, 438, 440; 604/904, 385.02, 385.17; 229/87.05
See application file for complete search history.

(56) References Cited

U.S. PATENT DOCUMENTS

| 3,092,251 | A |   | 6/1963  | Jaggers |
|-----------|---|---|---------|---------|
| 3,135,262 | A | * | 6/1964  | Werner et al. ......... 604/385.18 |
| 3,345,918 | A | * | 10/1967 | Simeone ................... 493/344 |
| 3,777,632 | A |   | 12/1973 | Pepmeier |
| 3,814,099 | A | * | 6/1974  | Kobler .................. 604/385.18 |
| 4,312,348 | A |   | 1/1982  | Friese |
| 4,610,659 | A |   | 9/1986  | Friese |
| 5,000,315 | A | * | 3/1991  | Butler ..................... 206/229 |
| 5,116,140 | A |   | 5/1992  | Hirashima |
| 5,134,832 | A |   | 8/1992  | Pesendorfer et al. |
| 5,411,202 | A | * | 5/1995  | Fenini ..................... 229/87.05 |
| 5,471,820 | A |   | 12/1995 | Oppe et al. |
| 5,582,342 | A | * | 12/1996 | Jud ........................ 229/87.05 |
| 5,713,824 | A | * | 2/1998  | Drummond et al. ........ 493/301 |
| 6,131,736 | A |   | 10/2000 | Farris et al. |
| 6,183,457 | B1 |  | 2/2001  | Kuhn |
| 6,203,512 | B1 |  | 3/2001  | Farris et al. |
| 6,299,607 | B1 | * | 10/2001 | Osborn et al. ......... 604/385.02 |
| 6,478,763 | B1 |  | 11/2002 | Simonsen et al. |
| 6,955,665 | B1 | * | 10/2005 | Domeier et al. ....... 604/385.02 |

FOREIGN PATENT DOCUMENTS

| DE | 29620118 U1 | 4/1988 |
| DE | 100 41 020  | 3/2002 |
| EP | 0 213 241 A1 | 3/1987 |

(Continued)

OTHER PUBLICATIONS

PCT International Search Report dated Sep. 18, 2003.

*Primary Examiner*—Jila M. Mohandesi
(74) *Attorney, Agent, or Firm*—James E. Oehlenschlager; Kevin C. Johnson; Ingrid N. Hackett

(57) ABSTRACT

The present invention relates to a wrapper for individually packaging absorbent articles for personal hygiene, especially tampons. The wrapper of the present invention is provided with an opening means comprising a tear tape and a stopper, the tear tape is used for opening the wrapper and the stopper prevents the wrapper from becoming separated into more than two segments of wrapper material upon being opened.

6 Claims, 3 Drawing Sheets

FOREIGN PATENT DOCUMENTS

| | | |
|---|---|---|
| EP | 0 711 705 A2 | 5/1996 |
| EP | 1 010 622 A1 | 6/2000 |
| GB | 758 879 | 10/1956 |
| GB | 2 227 666 A | 8/1990 |
| WO | WO 84/02840 A1 | 8/1984 |
| WO | WO 99/26573 | 6/1999 |
| WO | WO 99/43556 | 9/1999 |
| WO | WO 00/59437 A1 | 10/2000 |

* cited by examiner

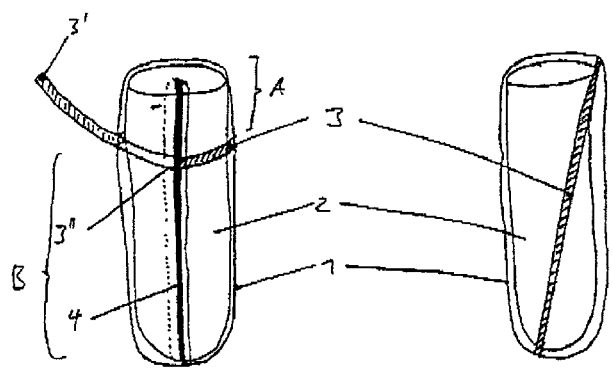
Fig. 1  Fig. 2
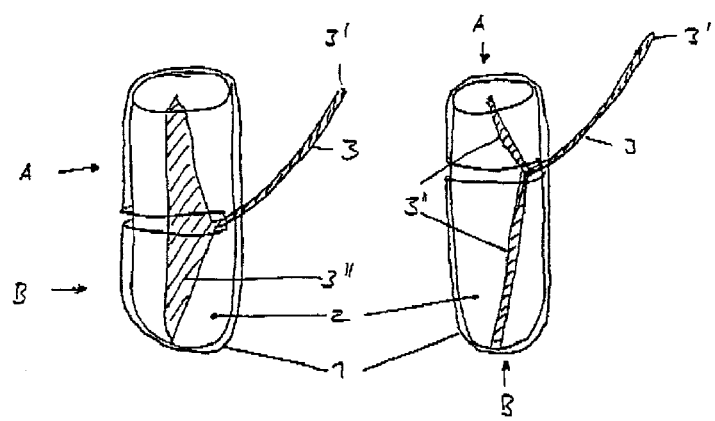 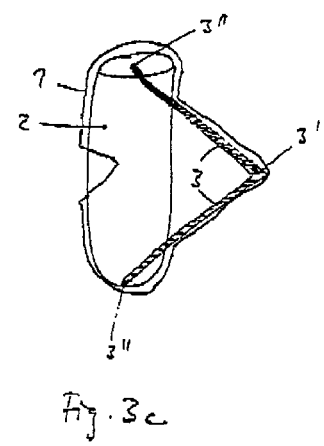
Fig. 3a  Fig. 3b  Fig. 3c

TAMPON WRAPPER WITH OPENING MEANS COMPRISING STOPPER

FIELD OF INVENTION

The present invention relates to a wrapper for individually packaging absorbent articles for personal hygiene, especially tampons. The wrapper of the present invention is provided with an opening means comprising a tear tape and a stopper, the tear tape is used for opening the wrapper and the stopper prevents the wrapper from becoming separated into more than two segments of wrapper material upon being opened.

BACKGROUND OF THE INVENTION

Absorbent articles for personal hygiene, especially those for feminine protection, are typically individually packaged for hygiene reasons. The packaging prevents the articles from being soiled, e.g. by dust, unintended touching and the like. Tampons are typically packaged individually into wrappers for guaranteeing hygienic conditions. These wrappers substantially enclose the tampon and consist in most cases of plastic film, such as films made of polyethylene, polypropylene or cellophane. The usual way of opening such wrappers in order to release the tampon for topical application is to separate the wrapper into multiple segments, whereby creating an opening in the wrapper, through which the tampon can be released. An example for such an opening mechanism is disclosed on EP-A-597,446. This document teaches an airtight tampon wrapper having a line of weakness extending around the whole circumference of the wrapped tampon. By acting on the wrapper on both sides of the line of weakness the wrapper is opened, whereby being separated into at least two non-connected parts. However, it is to be noted that the opening procedure for such a wrapper, namely twisting two sides of the wrapper against each other, needs some explanation; it is not intuitively operable by the user. Other known possibilities for opening tampon wrappers are associated to the use of tear tapes, i.e. tapes extending around the perimeter of the tampon and being situated between the tampon and the wrapper, which separate the wrapper into at least two segments of wrapper material upon pulling the tear tape. This generates at least three pieces of waste material, which are the two segments of the tampon wrapper and the tear tape itself. An exemplary execution of the aforementioned tear tape mechanism is realized in e.g. Tampax® and Always® digital tampons. However, tear tape opening means are very intuitively operable by users without further explanation, because pulling on a graspable end of a tear tape is very convenient and based on a very simple and intuitively understandable mechanism. Thus, opening means with tear tapes are highly desirable for commercial tampon wrappers.

All current methods for opening tampon wrappers have drawbacks. They are either not convenient enough or not intuitively operable by the user or they are generating many pieces of waste originating from the wrapper. These pieces have to be collected and disposed. Furthermore, it is inconvenient for the user of the tampon to handle three or more pieces of waste material originating from the tampon wrapper during the process of inserting a tampon. Thus, it would be beneficial to have a tampon wrapper fully enclosing an individual tampon in a hygienically satisfying manner, which wrapper can be conveniently and intuitively opened by using a tear tape and does not generate more than two pieces of material upon opening for releasing the tampon.

Accordingly, it is an object of the present invention to provide an improved tampon wrapper fulfilling the above requirements by being provided with an opening means comprising a tear tape and preventing the wrapper from becoming separated into more than two segments of wrapper material upon opening of said wrapper.

SUMMARY OF THE INVENTION

The tampon wrapper of the present invention, which is intended for being used for individually packaging of absorbent articles, in particular tampons, is provided with an opening means comprising a tear tape and a stopper, said stopper prevents the wrapper from becoming separated into more than two segments of wrapper material upon opening.

BRIEF DESCRIPTION OF THE DRAWINGS

FIG. 1 shows an exemplary wrapper 1 of the present invention, where the stopper is formed by a portion of the stopper end 3" of the tear tape 3 being attached to the wrapper material in a region of the wrapper material being partially coextensive with a seam 4 being generated during closing the wrapper 1.

FIG. 2 shows an exemplary wrapper 1 of the present invention, where the tear tape 3 extends around substantially the whole length of the wrapped tampon 2 and substantially around the whole perimeter of the wrapped tampon 2.

FIGS. 3a and b show exemplary wrappers 1 of the present invention, where the stopper is formed by the stopper end 3" of the tear tape, the stopper end 3" having a width of approximately the same extension as the length of the wrapped tampon 2. FIG. 3c shows an exemplary wrapper 1 of the present invention, where the stopper is formed by the stopper end 3", the stopper end 3" being constituted of two tear tapes being arranged in a V-shape fashion. The tear tapes can be connected to each other on at least one part.

DETAILED DESCRIPTION OF THE INVENTION

Figure 4A:
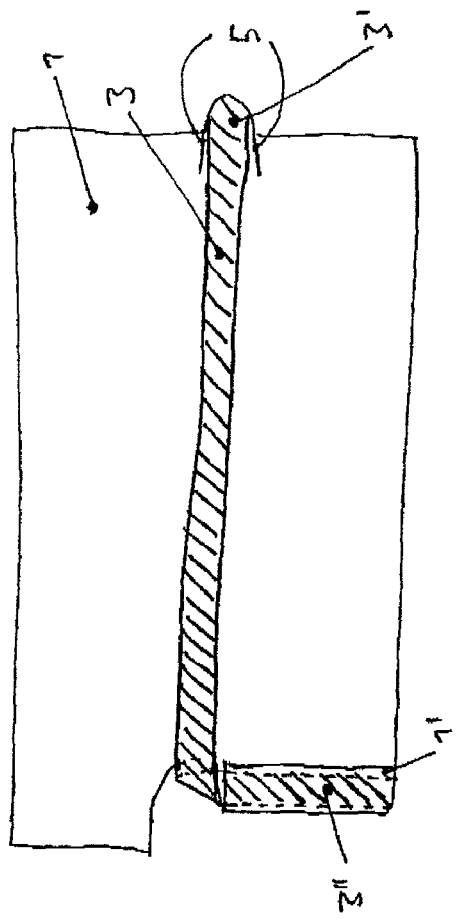
FIG. 4a shows an exemplary wrapper 1 of the present invention, where the stopper is formed by an overlapping portion 1' of the wrapper material occluding the stopper end 3" of the tear tape 3.

The present invention refers to a wrapper for individually packaging of absorbent articles, in particular of tampons for feminine hygiene.

By 'tampon' it is meant herein an absorbent article, in some embodiments a disposable one, comprising absorbent material usually being compressed into a self-sustaining, generally oblong, typically essentially cylindrical shape. In most cases the absorbent material comprises fibrous material, e.g. wood pulp fluff, cotton or the like. Tampons according to the present invention have an insertion end, a withdrawal end and a centre portion, said insertion end being opposed to said withdrawal end and said centre portion being located between said insertion end and said withdrawal end. In some embodiments the insertion end is tapered and the withdrawal end is flared. In some embodiments the tampon according to the present invention is also provided with a removal cord for allowing convenient removal of the used tampon from the region of use. The removal cord has two ends and is conventionally attached with one of said ends to the withdrawal end of the tampon, whereas the other end is referred herein as the free end. The removal cord can optionally be provided with a so-called secondary absorbent, which is a piece of absorbent material typically being located on the end of the removal cord being attached to the withdrawal end of the tampon. Secondary absorbents are used for absorbing fluid, which has leaked through or along the tampon and preventing this fluid from soiling the user's undergarments by flowing/being wicked along the removal cord. Tampons as used herein are suitable for various regions of use. The primary region of use is the female vagina, where the tampon is typically used for absorbing body fluids, especially menses. Typically, when being exposed to body fluids, the tampon will start to expand and thereby more or less lose its compressed self-sustaining shape. Another area of use involves other body cavities, where absorption of body fluids and/or application of medicine is intended, e.g. in the course of medical surgery. Tampon use is not only contemplated for human use, but can also be employed, particularly in administering medication, to other mammals.

The term 'use', as used herein, refers to the period of time that starts when the absorbent article is actually put in contact with the anatomy of the user.

By 'outer surface' of the tampon it is meant herein the visible surface of the compressed tampon prior to use or expansion.

By 'length' of a tampon it is meant herein the linear extension of a tampon along its largest dimension.

By 'perimeter' of a tampon it is meant herein the distance measured along the outer surface of the tampon in a portion of said outer surface extending in a plane being substantially perpendicular to the dimension of the length of said tampon. In other words, the length of the tampon extends along the x-axis of an orthogonal Cartesian coordinate system and the perimeter typically lies in the y,z-plane of said coordinate system. The perimeter of the tampon typically changes as a function of the length of said tampon.

'Wrapper' as used herein refers to a structure, which is formed of a wrapper material and which substantially encloses an individual absorbent article, in some embodiments an individual tampon for packaging purposes. The wrapper of the present invention is constituted of one connected piece of wrapper material, though a wrapper can be made from multiple pieces of material sufficiently joined together such that it substantially acts as one connected piece of wrapper material. The wrapper has two ends, each of them being assigned to an end of the wrapped tampon. The wrapper of the present invention has an opening means that allows opening of the wrapper for releasing the wrapped tampon. The opening means comprises a tear tape, which extends around the wrapped tampon by at least a part of the perimeter and/or at least a part of the length, and in some embodiments around the whole wrapped tampon perimeter-wise and/or length-wise. Even more in some embodiments, the tear tape according to the present invention extends around the whole perimeter of the wrapped tampon. The tear tape has a pulling end, which is graspable for the user. By pulling on the pulling end the tear tape tears opens the wrapper, thus allowing release of the tampon. Typically, when the tear tape extends around the whole perimeter and/or the whole length of the wrapped tampon, the tear tape separates the wrapper into at least two segments of wrapper material. The opening means of the present invention further comprises a stopper. The stopper prevents the separation of the tear tape from at least one of the segments of wrapper material, which are generated upon opening of the wrapper.

By 'wrapper material' it is meant herein any material suitable to be used for hygienically wrapping tampons. Said wrapper material has two surfaces; the 'inner surface' is directed towards the tampon being wrapped by the wrapper material wrapped, whereas the 'outer surface' is aligned opposite to said inner surface. Typically, suitable wrapper materials for use herein are flexible polymeric films, having a thickness of less than 1 mm. Examples for wrapper materials suitable for use with the present invention are polymeric films made of polyethylene, polypropylene, polyester, cellophane, polyamide, poly(vinyl chloride), ethylene-vinyl acetate copolymer and the like. Alternatively, heat-shrinkable films, stretch films or pre-stretched elastic material can be used to form the wrapper of the present invention. While not limited to a given composition, preferred compositions of heat-shrinkable and stretch films comprise primarily polyolefins such as polyethylene and polypropylene, or poly(vinyl chloride). Polystyrene and polyethylene-terephtalate (PET), although being not heat sealable, are also suitable for use with the present invention. Wrappers consisting of those materials can be closed by gluing with an adhesive. Other generally occlusive materials include metallic foils, such as aluminium foil. While occlusive wrapper materials are often preferred, in other situations non-occlusive or porous materials can be used, such as nonwovens, wovens, scrims, meshes and papers. Such non-occlusive materials can be made occlusive by combinations such as by lamination with or by coating with occlusive material. In the case of cellulosic papers, examples include lamination with a polymeric film such as a polyolefinic composition or coating or impregnation of the paper with wax. The aforementioned materials can be coated with various chemical compounds to improve their barrier properties or the ability for sealing. Any suitable combination of the aforementioned materials is also within the scope of the present invention. In some embodiments, the materials suitable for use as wrapper materials with the present invention are heat-sealable for forming the wrapper by closing the wrapper material via heat-sealing onto itself after having wrapped the tampon. Thereby a seam is generated in the regions of the wrapper, which were exposed to heat. Alternatives for closing the wrapper material are gluing, embossing, crimping, sewing, stitching, entangling, mechanical interlocking, cold pressure welding, or ultrasonic bonding. In some embodiments, the wrapper materials for use herein have a low flexural modulus for providing a low noise tampon wrapper during transport as well as during handling, i.e. opening of the wrapper.

The opening means of the present invention comprises a tear tape. 'Tear tape' as used herein means a strip of material in some embodiments having a higher tear-resistance than the wrapper material. The tear tape is usually a plastic film, though it could be made from other suitable materials such as paper, fabric, foils such as aluminium foil, etc. While the tear tape form is typically like a tape in form, i.e. thin, long and narrow, it can alternatively be in the form of a string, filament, rope, floss, thread, etc. Further, the tear tape can be partially comprised by a portion of the wrapper material itself so that the tear-tape portion of the wrapper material possesses a higher tear-resistance than the body of the wrapper material, e.g. by coating a portion of the wrapper or combining a portion of the wrapper with another element such as a string or filament. Another possibility of using a portion of the wrapper material as tear tape is to provide the wrapper material with two lines of perforation extending around the perimeter or along the length of the wrapped tampon, which are in some embodiments parallel, but can also be arranged differently, as long as they don't intercept each other. By pulling on the portion of wrapper material being located between the two lines of perforation said portion is torn from the remainder of the wrapper material, thereby creating an opening in the wrapper in the same way as a separate tear tape does. Typical plastic materials used for a tear tape are polyethylene, polypropylene, polyester, cellophane, polyamide, polyvinyl chloride, polystyrene and the like. The tear tape extends around the wrapped tampon by at least a part of the perimeter and/or at least a part of the length, and in some embodiments around the whole wrapped tampon perimeter-wise and/or length-wise. This means that the tear tape 3 can e.g. extend around the whole tampon 2 lengthwise or around the whole perimeter of the tampon or both, e.g. in a diagonal fashion as illustrated in FIG. 2. In a particularly preferred embodiment, the tear tape extends around the whole perimeter of the wrapped tampon only. The tear tape of the present invention has a length and a width and two ends, one pulling end 3', which extends beyond the outer surface of the wrapper material, and one stopper end 3". The length of the tear tape is defined by the linear extension of the tear tape in the direction of the tearing, which is initiated by pulling on the pulling end. The width of the tear tape is defined by its linear extension along the surface of the wrapped tampon perpendicularly the said length of said tear tape. The width of the tear tape can vary as a function of the length of the tear tape. The stopper end is attached to the wrapper material, either directly or via an additional piece of material. The tear tape, in some embodiments except said pulling end, is situated between the inner surface of the wrapper material and the outer surface of the wrapped tampon and is thus directly adjacent to the tampon.

The pulling end extends through the wrapper and is graspable for the user. By pulling the pulling end of the tear tape the wrapper material tears at the portion of the wrapper material being adjacent to the tear tape. Since the preferred tear tape extends around the whole wrapped tampon, this procedure separates the wrapper 1 into at least two segments (A and B). This is illustrated in FIGS. 1 and 3a and b. The tear tape is in some embodiments attached to the wrapper material, typically via combining the tear tape and the wrapper material with heat and pressure. Furthermore, the tear tape and the wrapper material can be attached to each other with an adhesive. Other means for attaching the tear tape to the wrapper material are e.g. ultrasonic bonding, mechanical interlocking, crimping, embossing or the like. In case the tear tape is constituted by a portion of the wrapper material as described above, the stopper end is constituted by the end of at least one of the lines of perforation or the region of higher tear resistance being adjacent to the stopper, while the other end of the portion of wrapper material used as tear tape forms the pulling end.

Figure 4D:
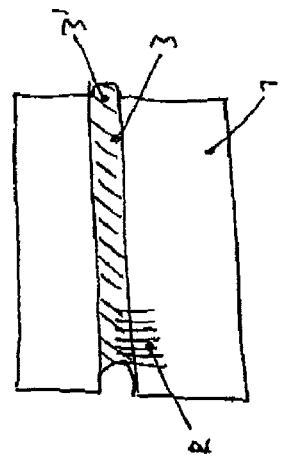
FIG. 4d shows an exemplary wrapper 1 of the present invention, where a region R of the wrapper material is modified to build a stopper.
Figure 4C:
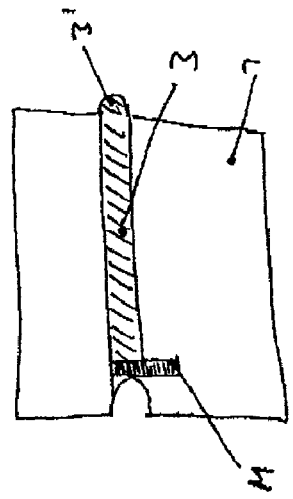
FIG. 4c shows an exemplary wrapper 1 of the present invention, where an additional piece of material M constitutes the stopper.

The opening means of the wrapper of the present invention is further provided with a stopper. 'Stopper' as used herein refers to a means for preventing full separation of the tear tape, in particular of the stopper end of the tear tape, from at least one of the segments of wrapper material generated upon opening of the wrapper, such as from at least one of segments A and B (see Figures). The stopper of the present invention can e.g. be constituted by the stopper end of the tear tape being bonded to the wrapper material, e.g. by heat or embossing, entangling, cold pressure welding or ultrasonic bonding. A particularly preferred execution of this embodiment is characterized in that the bonded portion of the stopper end 3" is substantially coextensive with at least a part of the seam 4 generated by bonding the wrapper material to itself in order to close the wrapper 1 around the tampon 2 as described hereinbefore. By this, the stopper can be made by the same process step which closes the wrapper 1. FIG. 1 illustrates this execution. A similar embodiment of the stopper of the present invention is characterized by the stopper end of the tear tape being attached to the wrapper material by an additional piece of material, e.g. a strip of plastic film, adhesive or the like. Alternatively, said additional piece of material can be applied on the opposite side of the wrapper material with respect to the stopper end 3" so that the stopper end 3" and the additional piece of material are separated by the wrapper material. In any case, the additional piece of material and the stopper end 3" are at least partially coextensive to each other. The additional piece of material can either be constituted of the same material as the tear tape or the wrapper material or can be constituted of a different material. The additional piece of material M is being bonded to the wrapper material and/or the tear tape, e.g. by heat or embossing, entangling, gluing, cold pressure welding or ultrasonic bonding. FIG. 4c illustrates this execution. Another embodiment of the stopper of the present invention is characterized in that a region of the wrapper material is modified, e.g. by mechanical interlocking, pressure, heat, ultrasonic bonding, folding, crimping, embossing and the like. Typically the stopper of such an embodiment constitutes a pattern in said region R, e.g. stripes, where the wrapper material modification was performed. Typically this pattern, e.g. stripes, is orientated to provide a stopper, which stops the tearing of the wrapper material and/or which changes the direction of the tearing. FIG. 4d illustrates this execution. When the tear tape is constituted of a portion of wrapper material, such as a portion between lines of perforation or a portion with higher tear resistance, the stopper can also be formed by bonding the stopper end of such tear tapes to a portion of wrapper material being outside the region of wrapper material being used as tear tape with an additional piece of material. Another possibility of forming a stopper for a tear tape being constituted of a portion of wrapper material between two lines of perforation is to provide both lines of perforations with different lengths, so that one is longer than the other, in order that the tearing stops on one of those lines earlier than on the other, thus preventing tearing off of the portion of wrapper material providing the tear tape from the reminder of the wrapper.

Another alternative embodiment of the stopper of the present invention, which is illustrated in FIGS. 3a–c, is a portion of the tear tape 3, in some embodiments a portion of the tear tape 3 being close to the stopper end 3", which has an increasing width towards the stopper end 3" of the tear tape 3 in a wedge-like fashion to have a width on the stopper end 3" of the tear tape 3 of approximately the same size as the length of the wrapped tampon 2. The stopper end 3" of this execution of the tear tape 3 is bonded to the wrapper material at both ends of the wrapper. This execution has the particular advantage of providing a wrapper 1 with a tear tape 3 opening means, which generates only one piece of waste material after being opened, because both segments of the wrapper material A and B generated by the tearing with the tear tape 3 and the tear tape 3 itself are still connected to the stopper end 3" of the tear tape 3 after the wrapper 1 was opened. A tear tape according to this embodiment can have e.g. a wedge-like (FIG. 3a) or Y-like (FIG. 3b) shape, both being oriented with the wider part on the stopper end of the tear tape. While it is preferred that a single piece of tear tape material be so shaped to provide a wider stopper end, it may be desirable for manufacturing reasons to combine two or more pieces of material to form a tear tape with a wider stopper end, as long as the pieces are sufficiently attached such that the tear tape acts as a single piece of connected material. Further, while it is preferred that the wider part of the tear tape should approximate the length dimension of the tampon, there can still be advantage with a width that is wider than the width of the tear tape near the pulling end (exclusive of any wider opening aid portion, such as a flap, that may be present for convenient grasping) while being less wide than the length of the tampon. Another possibility of providing an opening means suitable for this embodiment is to arrange at least two tear tapes in a V-like fashion, in some embodiments partially overlapping on the pulling end and in some embodiments being attached to each other on the pulling end, and are diverging from each other towards the stopper end of the V-shaped tear tape (FIG. 3c).

Figure 4B:
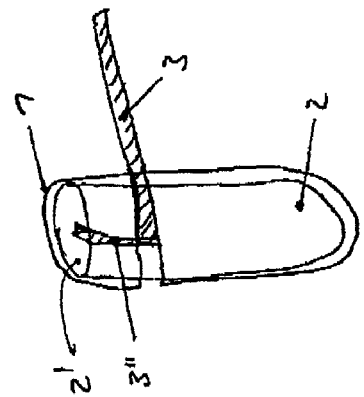
FIG. 4b shows an exemplary wrapper 1 of the present invention, where the stopper is formed by the stopper end 3" of the tear tape 3 having an increased width towards one end of the wrapper 1 in an L-like fashion, in particular towards the end of the wrapper 1 being assigned to the withdrawal end 2' of the tampon 2.

Another possibility of attaching the stopper end 3" of the tear tape 3 to the wrapper material is folding a portion 1' of the wrapper material over itself, thereby occluding said stopper end 3". The overlapping portion 1' of the wrapper material can then be bonded by e.g. embossing, crimping, mechanical interlocking, ultrasonic bonding, gluing, pressure and/or heat or any combination thereof, thereby the stopper end 3" of the tear tape 3 is attached to the overlapping portion 1'. By this, an exemplary L-shaped combination of tear tape and wrapper material can be created like shown in FIG. 4a. The tear tape of the embodiment in FIG. 4a is intended to extend around the perimeter of the tampon from the pulling end 3' to the beginning of the overlapping portion 1'. A further embodiment is shown in FIG. 4b. In this embodiment the tear tape 3 has an L-shape, wherein the tear tape 3, beginning from the pulling end 3' extends around the perimeter of the tampon 2. After having extended around substantially the whole tampon 2 the tear tape 3 turns towards the withdrawal end 2' of the tampon 2 and is attached with the stopper end 3" end to the end of the wrapper 1 being assigned to the withdrawal end 2' of the tampon 2. By this attachment of the stopper end the stopper is created for this embodiment.

It is preferred according to the present invention that the wrapper material tightly conforms to the outer surface of the wrapped tampon. This can be particularly well achieved by using heat-shrinkable or stretchable materials as wrapper material. 'Tightly conforming' of the wrapper to the outer surface of the wrapped tampon as used herein means that there is substantially no visually noticeable void space between the wrapper and the tampon. In other words, the perimeter of the tightly conforming wrapper on average exceeds the perimeter of the outer surface of the tampon by less about 50%, about 30%, about 10% or even about 5%. Since the perimeter of a tampon can typically change as a function of the length of said tampon, especially because the tampon has often an insertion end with a tip or has tails or indents in its outer surface, the aforementioned limits for the tight conformation of the wrapper apply to at least all substantially lengthwise portions of the outer surface of the tampon. In some embodiments of the present invention some regions of the wrapper material may provide additional functional benefits, such as cord deployment means. In these regions the wrapper material may not tightly conform to the outer surface of the tampon according to the definition herein. However, according to the present invention the wrapper material tightly conforms to at least about 70%, at least about 80% or even at least about 90% to the lengthwise portions of the outer surface of the tampon. As an example, the aforementioned perimeters of the wrapper and the tampon can be measured along the length of the tampon in steps of every 10% of the length of the tampon. Tightly conforming wrappers can be of particular use when so-called shaped tampons are wrapped, i.e. tampons having tails, indents or the like on their outer surface. Since tampons are typically made by compressing fibrous absorbent material into a self-sustaining shape, the tightly conforming wrapper can optionally be used to act with a certain compressing force on the outer surface of the tampon, which will aid maintaining said self-sustaining shape, in particular in the tailed or indented regions of the outer surface of the tampon by counteracting the expansion of the compressed material.

'Heat-shrinkable' as used herein refers to materials, which have an extension in at least two dimensions, e.g. films or nonwovens, and which reduce their extension in at least one of said dimensions when being heated to an elevated temperature above normal storage or usage temperatures, but being lower than their melting temperature or being lower than their decomposition temperature in case the material decomposes prior to melting.

Optionally, the tampon wrapper of the present invention can comprise one or more opening aids. 'Opening aid' as used herein means any kinds of means for making it easier for the user to open the wrapper for releasing the tampon. This especially refers to flaps extending from the pulling end of the tear tape. 'Flap' as used herein means a portion of material protruding from the outer surface of the wrapper and being sufficiently large to be reliably grasped by the user, thus providing for example a tab, handle or grip function. Optionally, such a protruding portion can be stiffened for better gripability by e.g. by embossing with or without the addition of heat. Other opening aids for being used with the present invention are pieces of material being attached to the wrapper material and protruding from the outer surface of the wrapper material, such as by adding a coating, or adding an additional layer of material, which can be another material or the wrapper material itself. This of course also applies to opening aids extending from the pulling end of the tear tape. A good example of integrally stiffening the protruding portion is by folding the material of said protruding portion over itself and then heat-seal it together.

In some embodiments, at both sides of the pulling end of the tear tape the wrapper material is weakened. The weakening of the wrapper material can be done by slitting the material, or applying a score line or perforation. The typical length of this weakness line is less than 1 cm. By pulling the pulling end of the tear tape the wrapper material tears at the portion of the wrapper material being adjacent to the tear tape where the weakness lines are applied. In the embodiment of the present invention being illustrated in FIG. 4 the wrapper material is provided with slits 5 on at least one side of the pulling end 3' of the tear tape 3. These slits 5 are e.g. 2 mm long and being situated in close proximity to the tear tape 3 in the region of the wrapper material, where the tearing process of the wrapper material, which is facilitated by the tear tape 3, starts. The slits 5 are decreasing the force required for tear initiation and thus make the opening of the wrapper 1 even more convenient.

Figures 5A, 5B:
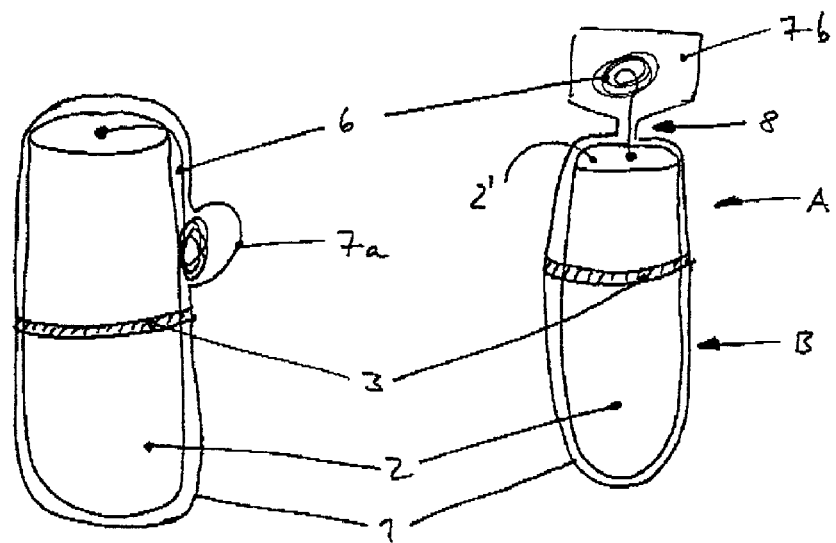
FIGS. 5a and b show exemplary wrappers 1 of the present invention having cord deployment means constituted by the wrapper material.

'Cord deployment means' as used herein refers to constructions for locating at least a portion of the removal cord of the tampon. In some embodiments, cord deployment means are also spacing away at least a portion of the removal cord from the surface of the tampon. By this, the user can better grasp the removal cord when applying the tampon compared to conventionally wrapped tampons, where the removal cord is always very tightly pressed onto the outer surface of the tampon and therefore being difficult to grasp. An example of the cord deployment means according to the present invention is illustrated in FIG. 5*a*, where a portion of the wrapper 1, which does not tightly conform to the outer surface of the tampon 2, forms a pocket 7 for containment of the removal cord 6. Alternative cord deployment means are shown in FIG. 5*b*, where a portion of the wrapper 1 extends beyond the withdrawal end 2' of the tampon 2. At least a part of the wrapper material extending beyond the withdrawal end 2' is compressed in a compressed zone 8. The removal cord 6 extends through the compressed zone 8, thereby getting attached to a certain degree to the wrapper 1 in said compressed zone 8. After opening of the wrapper 1 through pulling on the tear tape 3 and subsequent pulling on wrapper segment A for releasing the tampon 2 the compressed zone 8 is withdrawn from the tampon 2 and thereby also the removal cord 6 is pulled away from the tampon 2, which aids the removal cord 6 to be grasped by the user. The compressed zone 8 can be made by application of pressure and optionally heat to at least a part of the portion of the wrapper material extending beyond the end of the tampon 2. In EP-A-965,316 a method of heat sealing of the free end of the removal cord to the bottom of the tampon wrapper is disclosed, which also leads to loosening the free end of the removal cord from the tampon for better gripability. In this context it is preferred by the present invention that the attachment of the portion of the removal cord, which is extending through the compressed zone to said compressed zone is primarily achieved by frictional forces. Alternatively, if an opening aid is employed, it can also be constructed such that it retains in later-releasable fashion a portion of the cord to cause spacing away of at least a portion of the removal cord from the surface of the tampon (see e.g. FIG. 5*b*).

Figure 6:
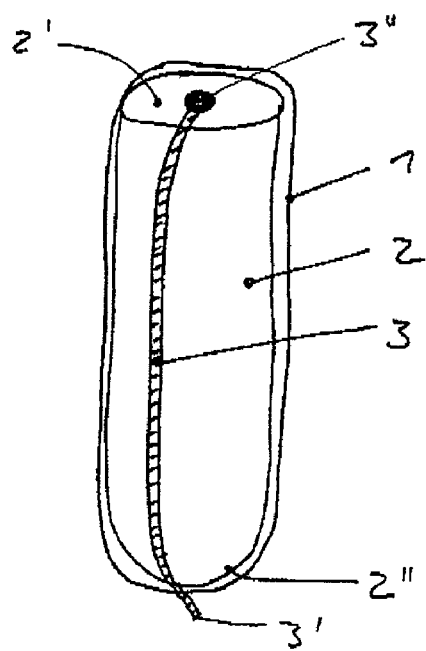
FIG. 6 shows a wrapper 1 according to the present invention having a tear tape 3 extending lengthwise only on one side of the wrapped tampon 2. This is an example for a tear tape 3, which is not extending around the whole length and/or perimeter of the wrapped tampon 2.

As said hereinbefore, it is preferred that the tear tape according to the present invention extends around the whole perimeter and/or the whole length of the wrapped tampon. However, there are also applications where a tear tape extending only around a part of the perimeter and/or length of the wrapped tampon is beneficial. In FIG. 6 such an embodiment is illustrated. The tear tape 3 of the wrapper 1 extends along the length on only one side of the wrapped tampon 2 and has a length, which approximately equals the length of the wrapped tampon, so that the tear tape 3 in FIG. 6 approximately extends from the insertion end 2" to the withdrawal end 2' of the wrapped tampon 2. By pulling on the pulling end 3' of the tear tape 3 the wrapper 1 is opened along the length of the tampon 2. Since the tear tape 3 is bonded to the wrapper 1 on the end of the wrapper 1 being assigned to the withdrawal end 2' of the wrapped tampon 2, the tear tape 3 will not separate from the wrapper 1 after the wrapper 1 was opened for releasing the tampon 2. A particularly preferred way of bonding the stopper end 3" of the tear tape 3 to the end of the wrapper 1 is folding the stopper end 3" into the wrapper material, which is folded itself in the wrapper ends in order to close the wrapper. The resulting entangling effect is strong enough to prevent separation of the stopper end 3" from the wrapper material on the respective end of the wrapper 1. This execution has the particular advantage that the opened wrapper is only constituted of one connected piece of material. It is to be noted that in this embodiment, despite shown differently in FIG. 6, the pulling end of the tear tape can also be located at the withdrawal end of the wrapped tampon while the stopper end of the tear tape is then located at the insertion end of the wrapped tampon.

Generally, the wrapper of the present invention in its most generic form can be made by wrapping wrapper material together with the tear tape, in separate steps, i.e. first the tear tape and then the wrapper material, or simultaneously, around the tampon and sealing the wrapper material onto itself in an overlapping portion for closing the wrapper material in order to form a tube of wrapper material. The sealing is in some embodiments facilitated by pressure and optionally heat, but also gluing, mechanical interlocking or the like are possible. Alternatively, the wrapper material can be sealed to itself to form a tube by bringing two portions of the wrapper material together then creating a cut seal, such as by use of a hot knife edge or impulse heat seal wire, such that a narrow, weld-like seam is created. The tube of wrapper material is then closed at one end and the tampon inserted from the other end. The preferred way of making a wrapper according to the present invention is to attach the tear tape to the wrapper material, e.g. by heat- or pressure bonding or by gluing, prior to forming the tube of wrapper material. The stopper can be made at any stage of the wrapper-making process, such as before or after wrapping the tampon. In order to achieve tight conformation of the wrapper material to the tampon it is preferred to use shrinkable, especially heat-shrinkable, material, which is shrunk after being closed around the tampon, in order in decrease the dimensions of the wrapper material, so that the wrapper tightly conforms to the outer surface of the tampon. The same can be achieved by using pre-stretched elastic material, which is allowed to relax into a non-tensed or non-stretched state after being closed around the tampon. Another alternative for achieving tight conformation of the wrapper to the outer surface of the tampon is partially closing the wrapper after having wrapped the wrapper material around the tampon, then evacuating the interior of the wrapper by application of vacuum and finally completely closing the wrapper.

Despite the fact that the present invention has been illustrated hereinbefore exclusively by examples for use as so-called digital tampons, i.e. tampons for use without applicator, the present invention is also applicable to applicator tampons.

While particular embodiments of the present invention have been illustrated and described, it would be obvious to those skilled in the art that various other changes and modifications can be made without departing from the scope of the invention. It is therefore intended to cover in the appended claims all such changes and modifications that are within the scope of this invention.

What is claimed is:

1. A combination of a wrapper and an individual tampon for feminine hygiene, said tampon having an insertion end, a withdrawal end, a centre portion, an outer surface, a length and a perimeter, said insertion end being opposed to said withdrawal end and said centre portion being located between said insertion end and said withdrawal end, said wrapper being constituted of one connected piece of wrapper material having an inner surface directed towards said tampon and a outer surface being aligned opposite to said inner surface, said wrapper substantially enclosing said tampon, said wrapper having two ends, one being assigned to said insertion end of said tampon and one being assigned to said withdrawal end of said tampon, said wrapper having an opening means, said opening means allowing opening of said wrapper for releasing said tampon, said opening means comprising a tear tape and a stopper, said tear tape extending around the tampon by at least one of; extending around the whole perimeter of said tampon, extending around the whole tampon length-wise or extending around the whole tampon in a diagonal direction, at least a portion of said tear tape being located between said outer surface of said tampon and said inner surface of said wrapper material, said tear tape having a stopper end and a pulling end, said wrapper being separated into two segments of wrapper material upon pulling on said pulling end of said tear tape, wherein said stopper prevents separation of said tear tape from one of said segments of wrapper material generated upon opening of said wrapper.

2. The combination of a wrapper and a tampon according to claim 1, wherein the perimeter of said wrapper exceeds said perimeter of said tampon by less than 50%.

3. The combination of a wrapper and a tampon according to claim 1, wherein said wrapper material is wrapped around said tampon and is bonded onto itself in an overlapping portion or by a narrow, weld-like fashion in order to close said wrapper material for substantially enclosing said tampon, whereby a seam is generated in the bonded portions of the wrapper material.

4. The combination of a wrapper and a tampon according to claim 1, wherein said stopper is constituted by said stopper end of said tear tape, said stopper end being attached to a portion of said wrapper material by heat sealing.

5. The combination of a wrapper and a tampon according to claim 1, wherein said wrapper material comprises a flexible material having a thickness of less than about 1 mm.

6. The combination of a wrapper and a tampon according to claim 1, wherein said wrapper material is selected from polymeric films made of polyethylene, polypropylene, polyester, cellophane, polyamide, poly(vinyl chloride), ethylene-vinyl acetate copolymer, polystyrene and polyethylene-based esters like polyethylene-terephtalate, heat shrinkable material, stretch foils, pre-stretched elastic material, cellulosic papers or metallic foils or combinations thereof.

* * * * *